US010188545B2

(12) United States Patent
Conti

(10) Patent No.: US 10,188,545 B2
(45) Date of Patent: Jan. 29, 2019

(54) FLEXIBLE CONE-SHAPED INTRA-VAGINAL SUPPORT DEVICE

(71) Applicant: Watkins-Conti Products, Inc., Edmond, OK (US)

(72) Inventor: Allison Conti, Edmond, OK (US)

(73) Assignee: WATKINS-CONTI PRODUCTS, INC., Edmond, OK (US)

( * ) Notice: Subject to any disclaimer, the term of this patent is extended or adjusted under 35 U.S.C. 154(b) by 207 days.

(21) Appl. No.: 15/242,105

(22) Filed: Aug. 19, 2016

(65) Prior Publication Data

US 2017/0049609 A1 Feb. 23, 2017

Related U.S. Application Data

(60) Provisional application No. 62/283,092, filed on Aug. 20, 2015.

(51) Int. Cl.
*A61F 6/12* (2006.01)

(52) U.S. Cl.
CPC ........ *A61F 6/12* (2013.01); *A61F 2230/0067* (2013.01)

(58) Field of Classification Search
CPC .......................... A61F 6/12; A61F 2230/0067
(Continued)

(56) References Cited

U.S. PATENT DOCUMENTS 1,996,242 A  4/1935 Hagedorn
2,534,900 A 12/1950 Chalmers
(Continued)

FOREIGN PATENT DOCUMENTS

DE  202009008893 U1  6/2009
DE  20 2017 106 300 U1  11/2017
(Continued)

OTHER PUBLICATIONS

English Translation of Kruger, Julia (DE 202009008893 U1) (attached as DE 202009008893EnglishTranslationNPL), Kruger Julia, Nov. 5, 2009.*
(Continued)

*Primary Examiner* — Navin Natnithithadha
*Assistant Examiner* — Sunita Reddy
(74) *Attorney, Agent, or Firm* — Venable LLP; Michele V. Frank

(57) ABSTRACT

In accordance with embodiments of the present disclosure, a flexible and non-absorbent vaginal insert device shaped to be held securely in place in a vagina when inserted, so as to improve symptoms associated with pelvic organ prolapse or urinary incontinence or both, is provided. The device is designed to be relatively easy to insert and remove. An applicator may be used to aid with insertion. The vaginal insert device comprises an upper portion, having a cone-shaped body, having a circular transverse cross-section throughout its length, having a wall with an interior side and an exterior side, an upper open end, a lower end, and a hollow interior, wherein the upper open end of the upper portion is the innermost portion of the device during insertion, and wherein the wall of the upper portion can be squeezed to make the upper portion more compact for easier insertion of the device, and wherein after insertion the wall expands back to its original shape. The device further comprises an exterior rim surrounding and protruding from the exterior side of the wall and being adjacent to the upper open end, and a plurality of ridges surrounding and protruding from the exterior side of the wall, and a removal portion extending from said lower end of said upper portion to assist in removal of the device. The device can also comprise one or more ventilation openings.

31 Claims, 16 Drawing Sheets

(58) Field of Classification Search
USPC .................................................. 600/29–32
See application file for complete search history.

(56) References Cited

U.S. PATENT DOCUMENTS

| | | | |
|---|---|---|---|
| 2,613,670 A | 10/1952 | Sokolik | |
| 2,638,093 A | 5/1953 | Kulick | |
| 2,763,265 A | 9/1956 | Waters | |
| D222,013 S | 9/1971 | Thomas et al. | |
| 3,626,942 A | 12/1971 | Waldron | |
| 3,845,766 A | 11/1974 | Zoller | |
| D250,049 S | 10/1978 | Hite, Jr. | |
| 4,286,593 A | 9/1981 | Place et al. | |
| D306,347 S | 2/1990 | Gyurik | |
| D323,212 S | 1/1992 | Crawford | |
| 5,827,248 A | 10/1998 | Crawford | |
| D430,669 S | 9/2000 | Buck et al. | |
| 6,170,484 B1 | 1/2001 | Feng | |
| 6,413,206 B2 | 7/2002 | Biswas | |
| 6,503,190 B1 | 1/2003 | Ulmsten et al. | |
| 6,558,370 B2 | 5/2003 | Moser | |
| 6,733,438 B1 | 5/2004 | Dann et al. | |
| 6,746,432 B2 | 6/2004 | Zadini et al. | |
| 6,770,025 B2 | 8/2004 | Zunker | |
| 6,773,421 B2 | 8/2004 | Bosselaar et al. | |
| 7,771,344 B2 | 8/2010 | Ziv | |
| 7,779,843 B2 | 8/2010 | Astani et al. | |
| 7,892,163 B2 | 2/2011 | Bartning et al. | |
| D655,415 S | 3/2012 | Chaffringeon | |
| D661,390 S | 6/2012 | McLain | |
| D661,392 S | 6/2012 | McLain | |
| 8,302,608 B2 | 11/2012 | Harmanli | |
| 8,652,026 B2 | 2/2014 | Zunker | |
| 8,690,847 B2 | 4/2014 | Norman | |
| 8,795,248 B2 | 8/2014 | Shihata | |
| D717,950 S | 11/2014 | Agrawal | |
| D719,653 S | 12/2014 | Agrawal | |
| 8,911,344 B2 | 12/2014 | Altan et al. | |
| 8,926,493 B2 | 1/2015 | Karapasha | |
| 9,022,919 B2 | 5/2015 | Ellefson et al. | |
| D741,479 S | 10/2015 | Agrawal | |
| D746,452 S | 12/2015 | Petrova | |
| D760,897 S | 7/2016 | Teo | |
| 9,402,703 B2 | 8/2016 | Ziv et al. | |
| 9,408,685 B2 | 8/2016 | Hou et al. | |
| D767,759 S | 9/2016 | McMillon-Nixon | |
| 2003/0149334 A1 | 8/2003 | Ulmsten et al. | |
| 2007/0203429 A1 | 8/2007 | Ziv | |
| 2008/0077097 A1 | 3/2008 | Chambers et al. | |
| 2008/0149109 A1 | 6/2008 | Ziv | |
| 2009/0266367 A1* | 10/2009 | Ziv | A61F 2/005 128/834 |
| 2009/0283099 A1 | 11/2009 | Harmanli | |
| 2010/0145137 A1 | 6/2010 | Morgan | |
| 2011/0295058 A1 | 12/2011 | Henriksson et al. | |
| 2012/0259167 A1 | 10/2012 | Karapasha et al. | |
| 2014/0000628 A1* | 1/2014 | Avery, Jr. | A61F 13/55175 128/834 |
| 2014/0000629 A1* | 1/2014 | Durling | A61F 2/005 128/840 |
| 2014/0100416 A1* | 4/2014 | Durling | A61F 2/005 600/29 |
| 2014/0100417 A1* | 4/2014 | Durling | A61F 2/005 600/30 |

FOREIGN PATENT DOCUMENTS

| | | |
|---|---|---|
| ES | 1064610 U | 4/2007 |
| GB | 2364645 A | 6/2002 |
| IN | 6032/CHE/2015 | 5/2017 |
| KR | 30-0707596 S | 11/2013 |
| KR | 30-0914045 S | 7/2017 |
| KR | 30-0914047 S | 7/2017 |
| WO | 2007/082341 A1 | 7/2007 |
| WO | 2011/013954 A2 | 2/2011 |
| WO | 2012/006670 A1 | 1/2012 |
| WO | 2013/108249 A1 | 7/2013 |
| WO | 2014/015975 A1 | 1/2014 |
| WO | 2016149317 A1 | 9/2016 |
| WO | 2017/015767 A1 | 2/2017 |

OTHER PUBLICATIONS

International Search Report and Written Opinion, International Application No. PCT/EP2016/062862, dated Nov. 17, 2016, 10 pages.

Written Opinion and International Search Report dated Nov. 17, 2016 in corresponding International Application No. PCT/US2016/047859 (9 pages).

Huang et al.; "Efficacy and Safety of Tension-Free Vaginal Tape-Secur Mini-Sling Versus Standard Midurethral Slings for Female Stress Urinary Incontinence: A Systematic Review and Meta-Analysis"; International Neurourology Journal, 2015, 19(4): pp. 246-258 (13 pages).

Ellington et al.; "Outcomes of Surgery for Stress Urinary Incontinence in the Older Woman"; Clin Geriatr Med., Nov. 2015, 31(4): pp. 487-505 (21 pages).

Jones et al.; "Pessary Use in Pelvic Organ Prolapse and Urinary Incontinence"; Reviews in Obstetrics & Gynecology, 2010, vol. 3, No. 1: pp. 3-9 (7 pages).

Petros et al.; "An Integral Theory and Its Method for the Diagnosis and Management of Female Urinary Incontinence"; Scandinavian Journal of Urology and Nephrology; Suppl No. 153: 1993; pp. 1-93 (93 pages).

Coelho et al: "Introduction of the method of intravaginal culture (IVC), through the device INVOCell routine laboratory RHA in Brazil"; JBRA Assisted Reproduction 2013; vol. 17 (No. 6): pp. 340-343 (4 pages); published Jan. 2013; doi: 10.5935/1518-0557.20130076.

* cited by examiner

SECTION A-A

FLEXIBLE CONE-SHAPED INTRA-VAGINAL SUPPORT DEVICE

CROSS-REFERENCE TO RELATED APPLICATIONS

The present patent application claims priority to previously filed U.S. Provisional Patent Application Ser. No. 62/283,092, filed Aug. 20, 2015, the entirety of which is hereby incorporated by reference.

TECHNICAL FIELD

The present disclosure relates in general to a flexible and non-absorbent vaginal insert device for use in improving symptoms associated with pelvic organ prolapse and urinary incontinence when the device is inserted, and more particularly to a vaginal insert device that is easier to insert and remove.

BACKGROUND

Stress Urinary Incontinence (SUI) and Pelvic Organ Prolapse (POP) are growing problems globally that not only cost health care systems large amounts of money, but severely degrade the quality of life of tens of millions of women in the United States alone. Although surgical solutions can succeed in ameliorating symptoms associated with SUI and POP, surgery is not without risks and complications and may even leave the patient in a worse situation than before treatment. See Huang W, Wang T, Zong H, Zhang Y, *Efficacy and Safety of Tension-Free Vaginal Tape-Secure Mini-Sling Versus Standard Midurethral Slings for Female Stress Urinary Incontinence: A Systematic Review and Meta-Analysis*, International Neurourology Journal, 2015, 19(4):246-58, which is incorporated herein by reference. See also Ellington D R, Erekson E A, Richter H E, *Outcomes of Surgery for Stress Urinary Incontinence in the Older Woman*, Clin Geriatr Med., 2015, 31(4):487-505, which is incorporated herein by reference. The FDA has issued several Public Health Notifications regarding surgical mesh placed through the vagina (transvaginal placement) to treat POP and SUI. The FDA identified serious and frequent complications with surgical mesh, including mesh erosion through the vagina, pain, infection, bleeding, discomfort during intercourse, organ perforation, urinary problems, recurrent prolapse, neuro-muscular problems, vaginal scarring/shrinkage & emotional problems. Most surgical complications require intervention including medical, additional surgical treatment and hospitalization.

Prior art pessaries, which have been most commonly used for management of female POP but also have been used for SUI, have presented a viable non-surgical option for treating SUI and POP. These prior art pessaries have had few complications and side effects. However, these devices are traditionally placed in the vagina for an extended period of time. They may also be uncomfortable. Furthermore, these prior art devices have been difficult for the patient to insert and remove, and use, insertion and removal of these devices have often required regular office visits with a physician for years. See, Jones K A, Harmanli O, *Pessary Use in Pelvic Organ Prolapse and Urinary Incontinence*, Rev Obstet Gynecol, 2010, 3(1):3-9, which is incorporated herein by reference. Difficulty with self-removal and insertion of the pessary, having the pessary fall out during defecation, and lack of comfort and convenience may be limiting widespread use of the prior art devices.

Stress Urinary Incontinence (SUI) in women, is the involuntary leakage of urine due to a weakened pelvic support system and/or pressure on the bladder from aging, genetics, or childbirth. The Urology Care Foundation estimates that one of every three women will experience SUI at some point in their lifetime. There are a few types of urinary incontinence including stress incontinence, urge incontinence and mixed incontinence. All are mainly due to connective tissue laxity or damage in the vagina or supportive ligaments. See *An Integral Theory and Its Method for the Diagnosis and Management of Female Urinary Incontinence*, Petros P E, Ulmsten U I, Scand J Urol Nephrol Suppl, 1993, 153, 1-93, which is incorporated by reference. FIG. 1 is a cross-section of the pelvic region of a female with normal anatomy illustrating the uterus 10, cervix 12, bladder 14, urethra 16, vagina 18, and rectum 20. FIG. 2 illustrates urinary incontinence (i.e., leakage of urine) 22 caused by stress or pressure 24 on the bladder 14. Involuntary leakage of urine often occurs during activities such as coughing, laughing, sneezing, lifting or exercise.

Connective tissue damage to three zones of the Integral System, which encompasses all three pelvic organs, including the bladder, vagina and ano-rectum, is the ultimate cause of Pelvic Organ Prolapse (POP) and dysfunction in these organs. FIG. 3 is a cross-section of the pelvic region of a female with a prolapsed bladder 26. FIG. 4 is a cross-section of the pelvic region of a female with a prolapsed back-passage 28. FIG. 5 is a cross-section of the pelvic region of a female with a prolapsed uterus 30. POP is commonly due to child bearing but may also be caused simply by genetics and the aging process.

Therefore, there is a need for a pessary or other vaginal insert device that manages, improves, or eliminates female incontinence, POP or both incontinence and POP. There is a further need for such a pessary or other vaginal insert device that does not require a prescription, and is non-absorbent, over the counter, convenient, comfortable, and easy for a patient to insert and remove, with no or minimal physician intervention. Preferably such a vaginal insert device would also be reusable, but it also can be disposable.

SUMMARY

In accordance with the teachings of the present disclosure, the disadvantages and problems associated with prior art pessaries may be substantially reduced or eliminated.

In accordance with embodiments of the present disclosure, a vaginal insert device for use in improving symptoms associated with pelvic organ prolapse, urinary incontinence, or both pelvic organ prolapse and urinary incontinence can include an upper portion, which is made of an elastic and non-absorbent material, having a cone-shaped body, having a circular transverse cross-section throughout its length, having a wall with an interior side and an exterior side, an upper open end, a lower end, and a hollow interior, wherein the circumference of the upper portion decreases from the upper open end to the lower end, wherein the upper open end of the upper portion is the innermost portion of the vaginal insert device during insertion, and wherein the wall of the upper portion can be squeezed to make the upper portion more compact for easier insertion of the vaginal insert device, and wherein the wall expands back to its original shape after insertion. Such vaginal insert device can further include: an exterior rim surrounding and protruding from the exterior side of the wall of the upper portion and being adjacent to the upper open end; and a plurality of ridges surrounding and protruding from the exterior side of the wall of the upper portion and being spaced apart from the upper open end to the lower end.

In accordance with these and other embodiments of the present disclosure, a vaginal insert device can include a removal portion extending from the lower end of the upper portion, wherein the removal portion can be accessed from the exterior of a vagina when the vaginal insert device is inserted in the vagina, and wherein the removal portion assists in removal of the vaginal insert device from the vagina. The removal portion can comprise a string or a stem. In the embodiment where the removal portion is a stem, the stem can extend from the lower end of the upper portion, wherein the upper portion and the stem comprise an integral one-piece device made from the elastic and non-absorbent material, wherein the stem has a cone-shaped body, having a circular transverse cross-section throughout its length, having a wall, an upper end, a lower open end, and a hollow interior, and wherein the circumference of the stem increases from the upper end to the lower open end. The removal portion can also have a plurality of ridges like the upper portion.

In accordance with these and other embodiments of the present disclosure, a vaginal insert device can include one or more ventilation openings. A ventilation hole can be located at the point where the lower end of the upper portion and a stem intersect. One or more ventilation openings can also be located in the wall on the upper portion.

In accordance with these and other embodiments of the present disclosure, a vaginal insert device can include an exterior rim which is circular and has a first section and a second section, wherein the first section protrudes from the exterior side of the wall of the upper portion a greater distance than the second section.

In accordance with these and other embodiments of the present disclosure, a vaginal insert device can include an applicator used during insertion of the device, wherein the applicator can contain at least the upper portion when it is in a more compact shape, and wherein the applicator assists in the insertion of the device.

Medical and other advantages of the present disclosure may be readily apparent to one skilled in the art from the figures, description and claims included herein. The objects and advantages of the embodiments will be realized and achieved at least by the elements, features, and combinations particularly pointed out in the claims.

It is to be understood that both the foregoing general description and the following detailed description are examples and explanatory and are not restrictive on the claims set forth in this disclosure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Preferred embodiments and their advantages are best understood by reference to FIGS. 6A through 15C, wherein like numbers are used to indicate like and corresponding parts or sections.

The vaginal insert device of the present invention manages, improves, or eliminates female urinary incontinence, Pelvic Organ Prolapse (POP), or both POP and urinary incontinence. It does not require a prescription, and is non-implantable, non-absorbent, over the counter, convenient, flexible, comfortable, and easy for a patient to insert and remove, with no or minimal physician intervention. Preferably such a vaginal insert device would also be reusable, but it also can be disposable. It eliminates concern of Toxic Shock Syndrome (TSS) by not consisting of an absorbency element which could produce odor and breed bacteria. The device of the present invention is fabricated, such as by a molding process, with an elastic and non-absorbent material, preferably a biocompatible elastomer such as medical grade silicone. An example of a silicone material suitable for use in the present invention is NuSil Technology's MED-4950 product, which is characterized as a liquid silicone rubber.

The vaginal insert device of the present invention is shaped so that it is held securely in place in the vagina when inserted, as well as shaped to impose pressure on the urethral sphincter and to support pelvic organs. One exemplary use of the vaginal insert device of the present invention is for management of stress urinary incontinence (SUI) and the involuntary leakage of urine during activities such as coughing, laughing, sneezing, lifting and exercise for patients over the age of eighteen. It is expected that the device will typically be inserted by an adult woman for up to about twelve hours or more, depending on their comfort level.

Figure 1:
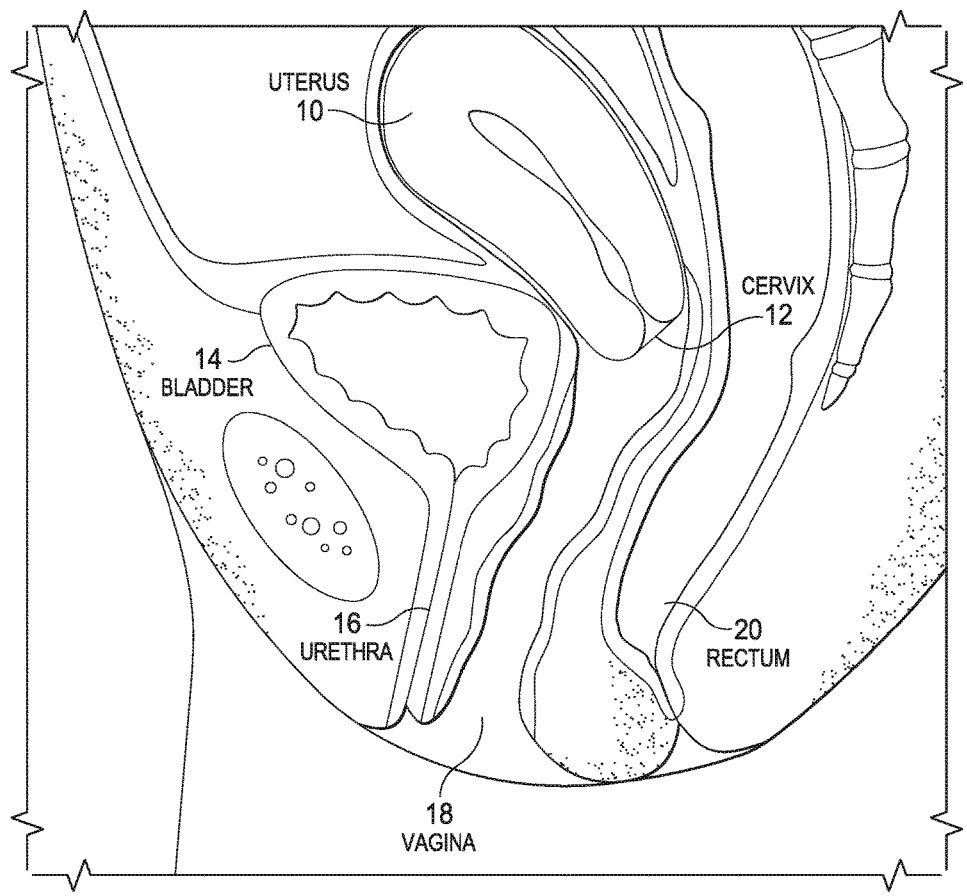
FIGS. 1-5 each illustrate a cross-section of the pelvic region of a female for purposes of discussing the background of the present disclosure.
Figure 2:
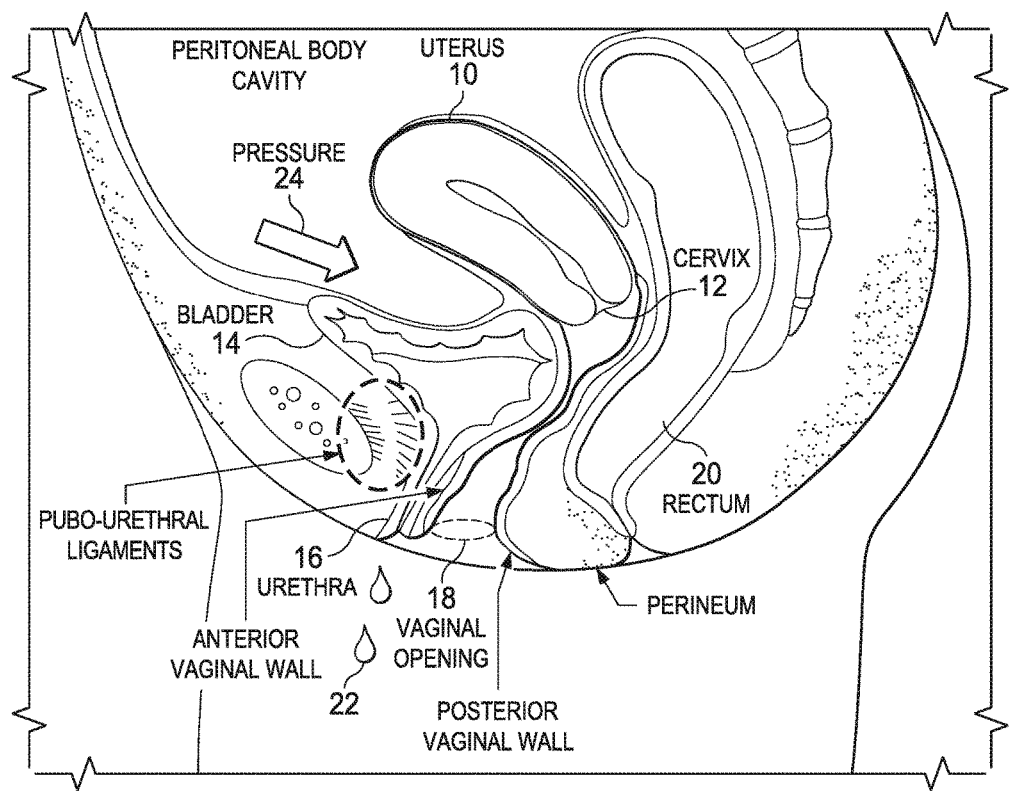
Figure 3:
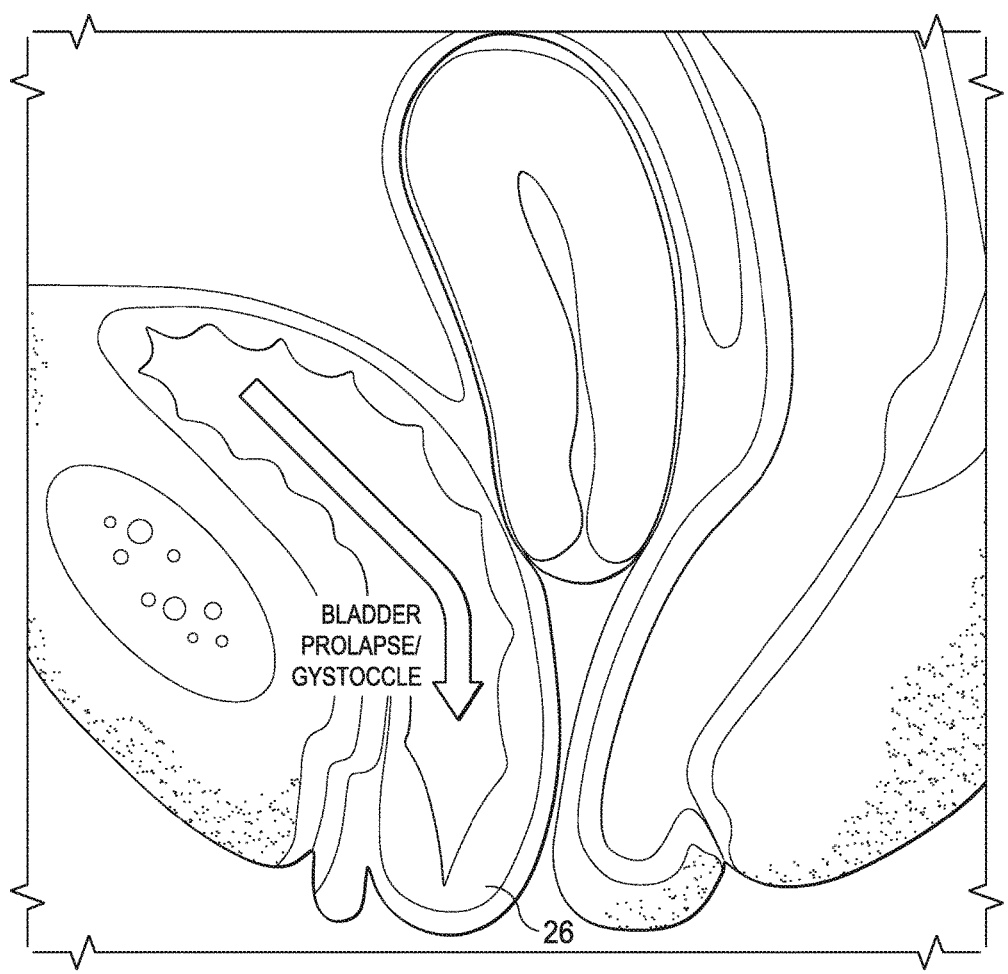
Figure 4:
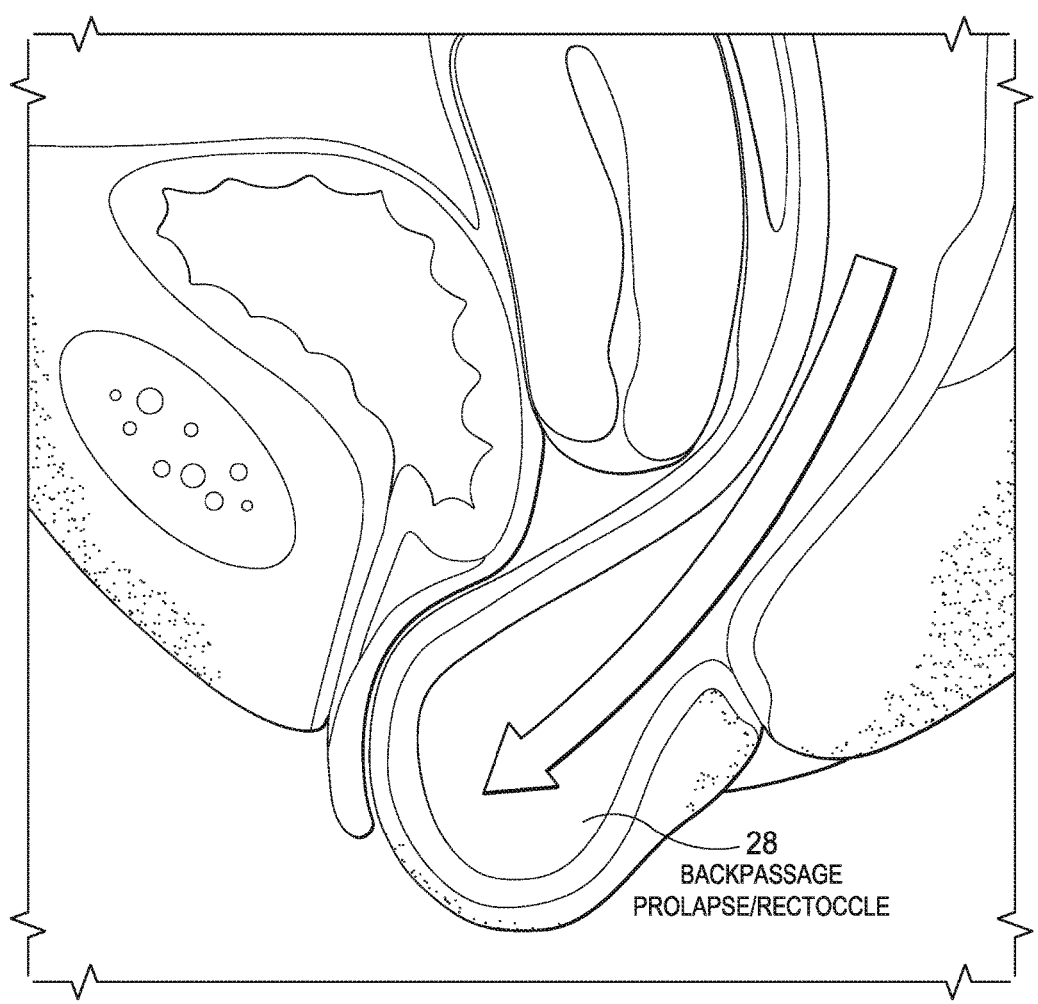
Figure 5:
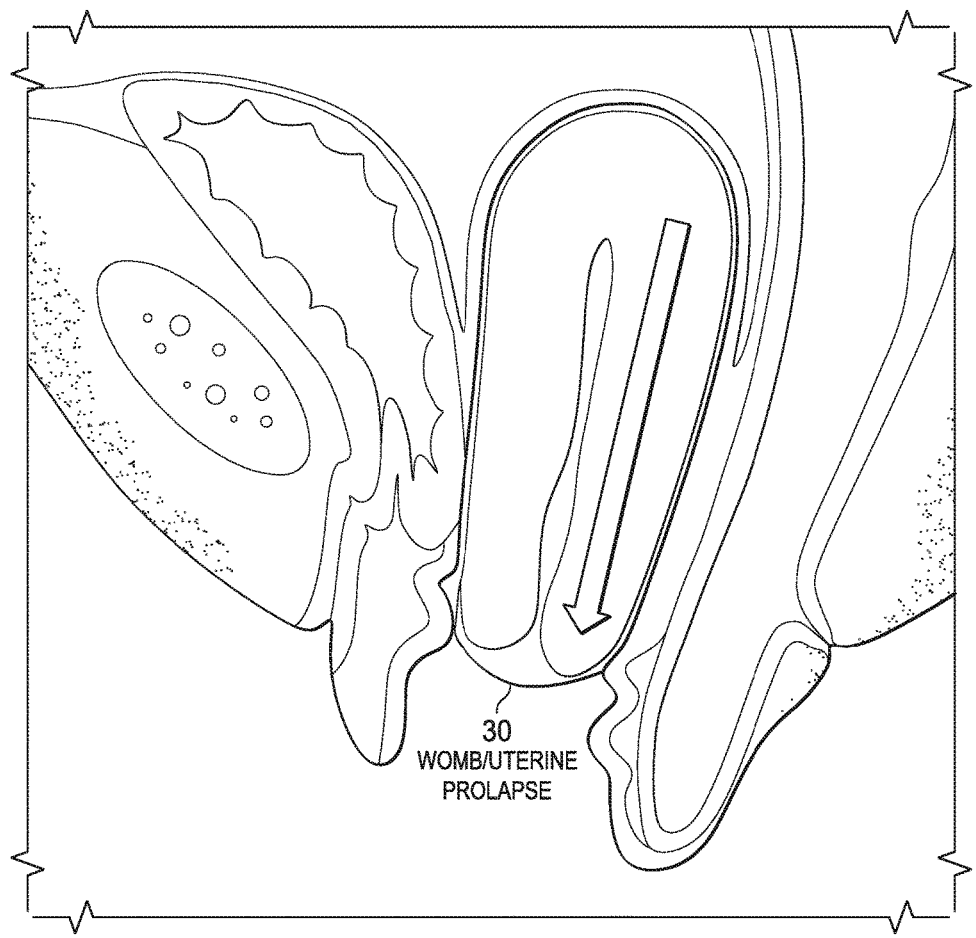
Figure 6A:
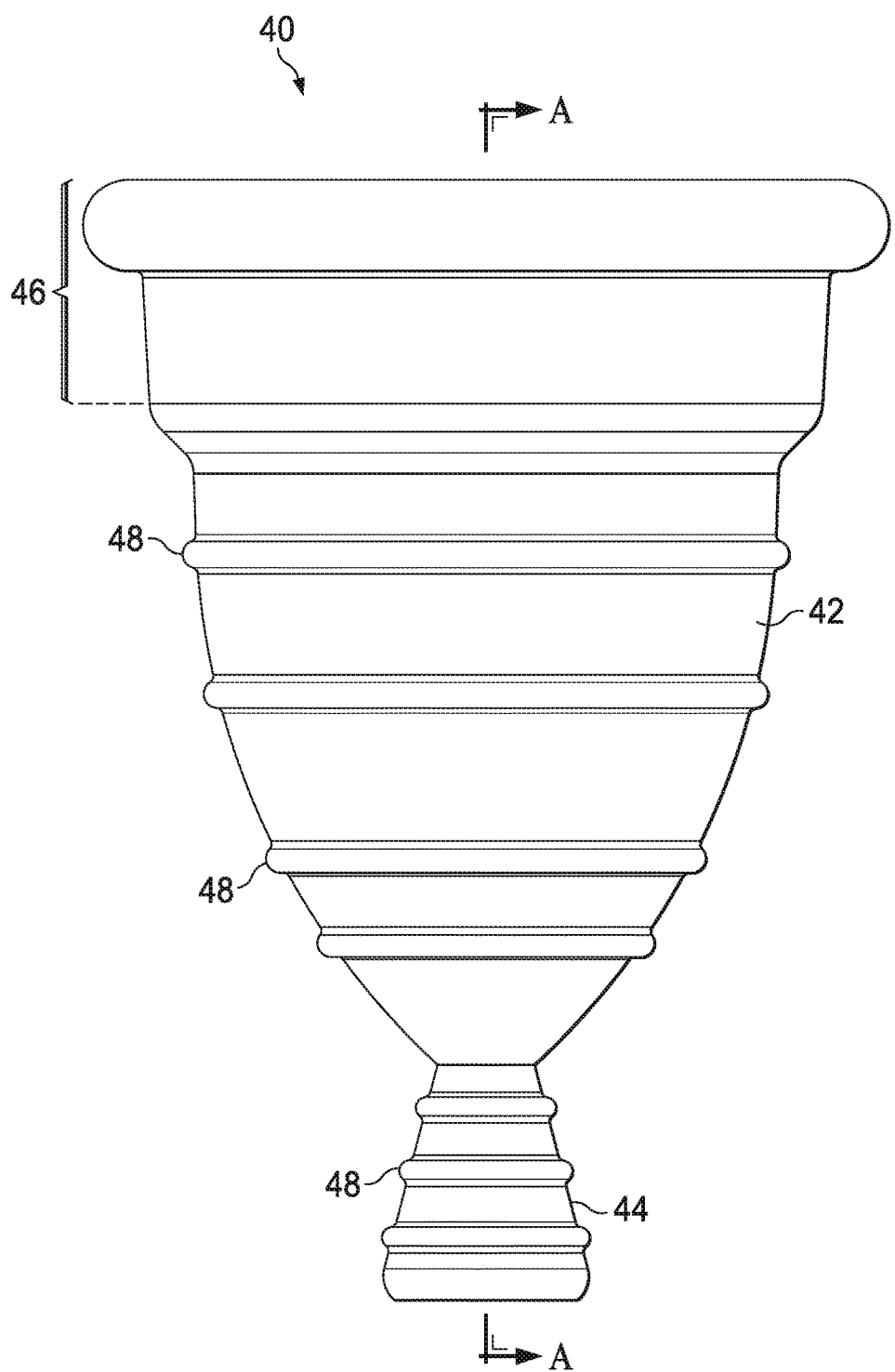
FIG. 6A illustrates a side view of an example vaginal insert device, in accordance with embodiments of the present disclosure.

FIG. 6A illustrates a side view of an example vaginal insert device 40, in accordance with embodiments of the present disclosure. The vaginal insert device 40 of FIG. 6A comprises an upper portion 42 and a lower, stem-like, removal portion 44. As further illustrated and described in more detail below, the upper portion 42 includes a rim 46 as well as ridges 48 which are preferably spaced apart from the top of the upper portion to the lower end of the upper portion. Ridges 48 can be randomly or uniformly spaced. The removal portion can also have ridges 48, which like the upper portion are spaced apart from the top of the removal portion to the lower end of the removal portion.

Figure 6B:
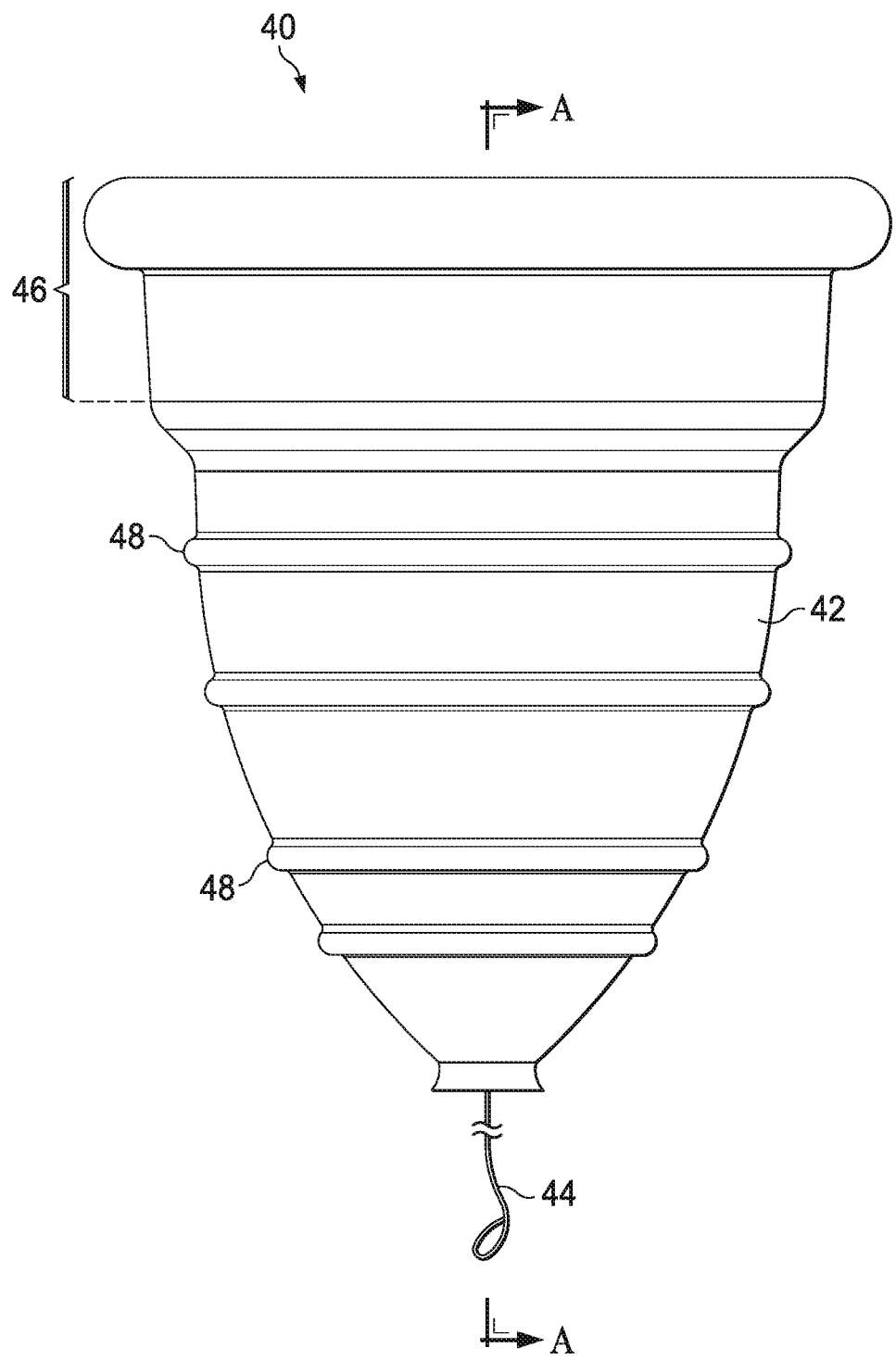
FIG. 6B illustrates a side view of another example vaginal insert device, in accordance with embodiments of the present disclosure.

FIG. 6B illustrates a side view of another example vaginal insert device 40, in accordance with embodiments of the present disclosure. In this embodiment, device 40 is the same as the embodiment shown in FIG. 6A except the removal portion 44 is a string, cord or ribbon (collectively referred to as "a string"), such as is used in removing a tampon.

Figure 7:
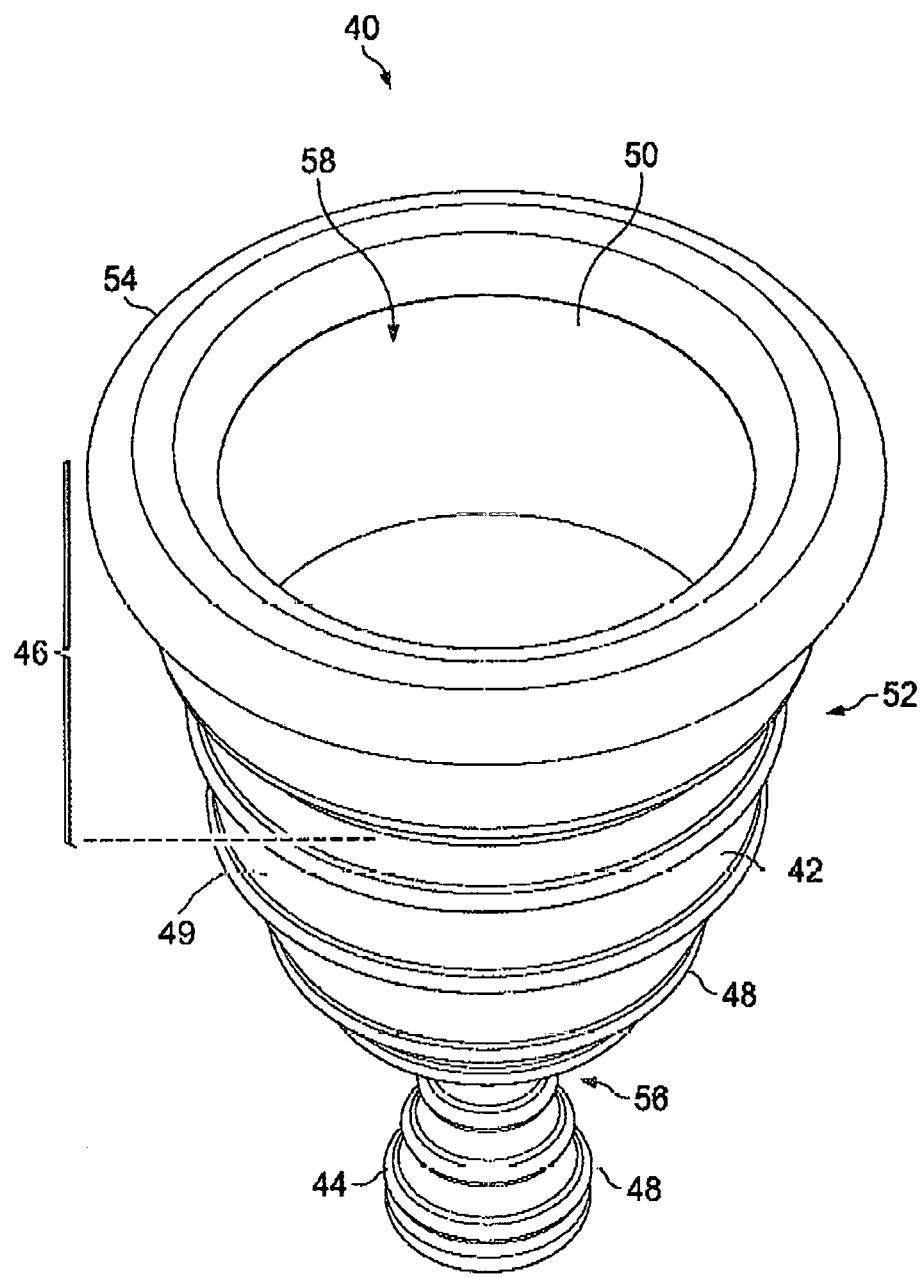
FIG. 7 illustrates a perspective view of the vaginal insert device of FIG. 6A.

FIG. 7 illustrates a perspective view of the vaginal insert device 40 of FIG. 6A. As shown in FIG. 7, the upper portion 42 has a cone-shaped body, having a circular transverse cross-section throughout its length, has a wall 49 with an interior side 50 and an exterior side 52, an upper open end 54, a lower end 56, and a hollow interior 58, wherein the circumference of the upper portion decreases from the upper open end to the lower end. As illustrated, rim 46 is preferably circular and surrounds and protrudes from the exterior side 52 of the wall and is adjacent to the upper open end 54. Ridges 48 are preferably circular rings which surround the exterior side 52 of wall 49. As further illustrated, a stem or removal portion 44 extends from the lower end 56 of the upper portion 42. The upper portion 42 and the stem 44 can be fabricated as an integral one-piece device. The upper portion, with the rim and the plurality of ridges, holds the vaginal insert device securely in place to impose pressure on the urethral sphincter, or to support pelvic organs, or to both impose pressure on the urethral sphincter and support pelvic organs, when the device is inserted. FIG. 7 also illustrates that the stem 44 can have a cone-shaped body.

Figure 8:
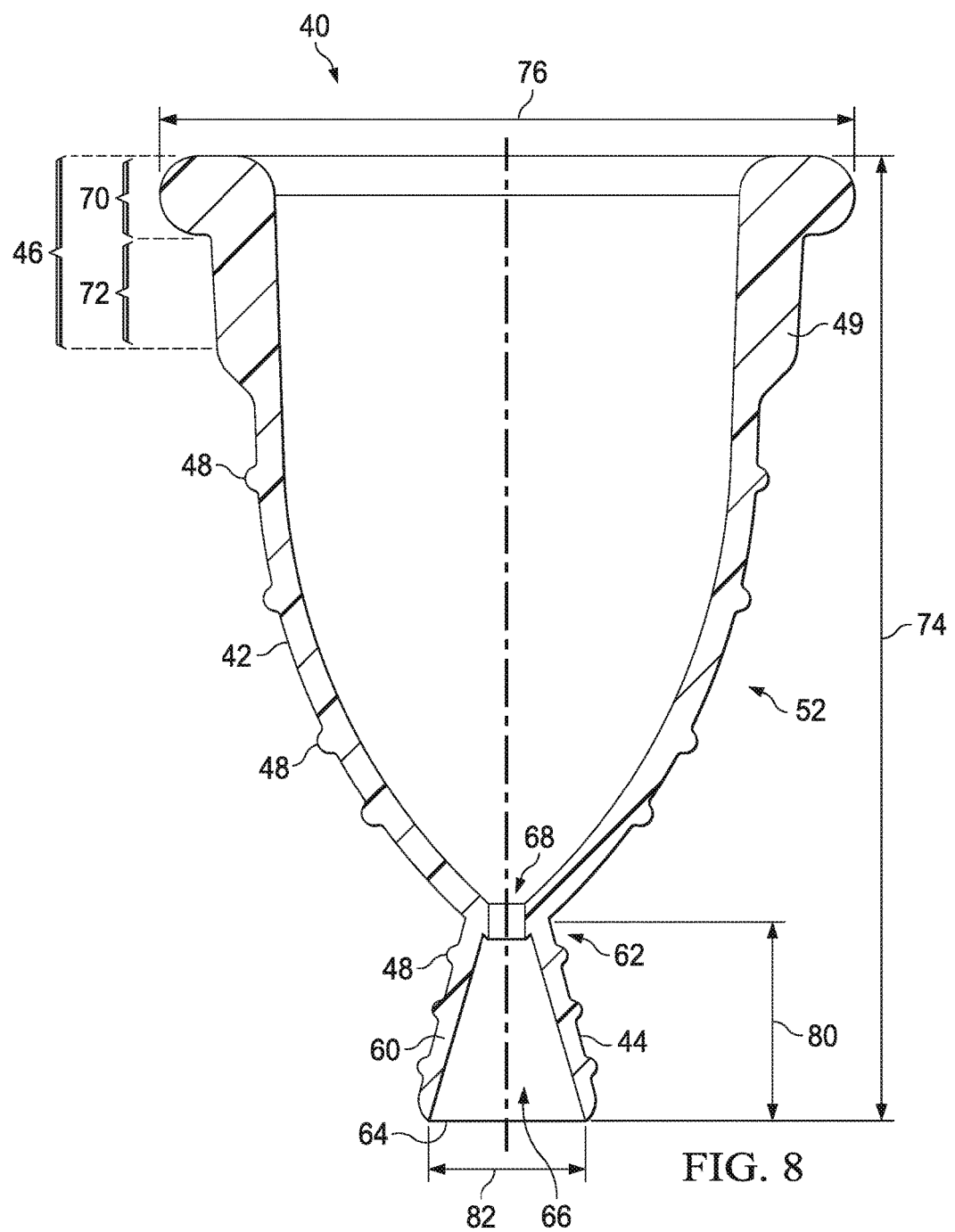
FIG. 8 is a cross-sectional view of vaginal insert device of FIG. 6A across section line A-A.

FIG. 8 is a cross-sectional view of vaginal insert device 40 of FIG. 6A across section line A-A. As shown in FIG. 8, stem 44 can have a circular transverse cross-section throughout its length, having a wall 60, an upper end 62, a lower open end 64, and a hollow interior 66, wherein the circumference of the stem increases from the upper end to the lower open end. As illustrated, ridges 48 protrude from the exterior side 52 of the wall 49.

FIG. 8 further illustrates an embodiment of vaginal insert device 40 which includes a ventilation opening 68. The ventilation opening can include a ventilation hole, a screen or a mesh or any other component with an opening. As would be understand by one of ordinary skill of the art, vaginal insert device 40 can include a plurality of ventilation openings in locations other than, or in addition to, ventilation opening 68, such as in wall 49 of the upper portion 42. The one or more ventilation openings are intended to make the vaginal insert device more comfortable for the patient when inserted. The one or more openings may also equalize the air pressure between the inside and outside of the vagina 18, when vaginal insert device 40 is inserted. However, having a ventilation opening is not required for the vaginal insert device to be comfortable, useful and effective.

FIG. 8 illustrates further detail regarding an embodiment where rim 46 has a first section 70 and a second section 72, both of which protrude from the exterior side 52 of the wall 49, with the first section protruding a greater distance than the second section.

A person of ordinary skill in the art would understand that multiple alternative embodiments of rim 46 are possible, including an embodiment in which rim 46 comprises just the first section 70, or another embodiment in which rim 46 comprises only one section but has a greater height than first section 70 and protrudes from the exterior side 52 of the wall the same distance from the top of the rim to the bottom of the rim. In another embodiment, rim 46 surrounds the exterior side 52 of the wall 49, adjacent to the upper open end 54, and comprises sections which protrude and sections which do not protrude from the exterior side of the wall.

With reference to FIGS. 7 and 8, the term "ridges" is intended to be broadly defined. Accordingly, ridges 48 can include the embodiment illustrated in FIGS. 7 and 8, in which ridges 48 are protrusions which are preferably circular rings which surround the exterior side of wall 49. However, "ridges" can also include any protrusions that extend from the exterior side 52 of wall 49, such as a plurality of studs or knobs.

A person of ordinary skill in the art would understand that the vaginal insert device 40 can come in different sizes, including different sizes to accommodate adult women with differing anatomy. Furthermore, a person of ordinary skill in the art would understand that the dimensions of the various sections and portions of the device 40 can be modified from the multiple embodiments illustrated and disclosed herein. For example, referring to FIG. 8, the total height 74 of device 40, diameter 76 at the upper open end 54 of the upper portion 42, and thickness of the wall 49 of the upper portion 42 of the device 40 can be modified, while retaining or improving on the intended usefulness, effectiveness and other benefits of the device. The following non-exclusive list of dimensions, in reference to FIG. 8, are non-limiting examples of embodiments of device 40 which are believed to be suitable for most women, and which provide the intended usefulness, effectiveness and other benefits of the device. For example, a suitable total height of device 40 is estimated to be in the range of about 58.0 to 67.0 millimeters (mm), and a suitable outer diameter 76 is estimated to be in the range of about 38.0 to 44.0 mm. A suitable height of the stem 44 is estimated to be in about the 13.0 to 15.0 mm range. A suitable thickness of the wall 49, in sections without ridges 48, of the upper portion 42, below rim 46, is estimated to be about 2.0 mm, whereas a suitable thickness of the wall 49, in sections with ridges is estimated to be about 2.5 mm Wall 60 of stem 44 is estimated to have a suitable thickness of about 1.25 mm in sections without ridges 48. A suitable height of rim 46 is estimated to be about 15.0 mm, with a suitable height of first section 70 estimated to be about 5.0 mm and a suitable height of second section 72 estimated to be about 10.0 mm. A suitable thickness of the first section 70 is estimated to be about 6.0 mm and the second section 72 is estimated to be about 4.0 mm A suitable outer diameter 82 of lower open end 64 is estimated to be about 10.5 mm. A suitable diameter of ventilation opening 68 is estimated to be about 2.0 mm.

Figure 9:
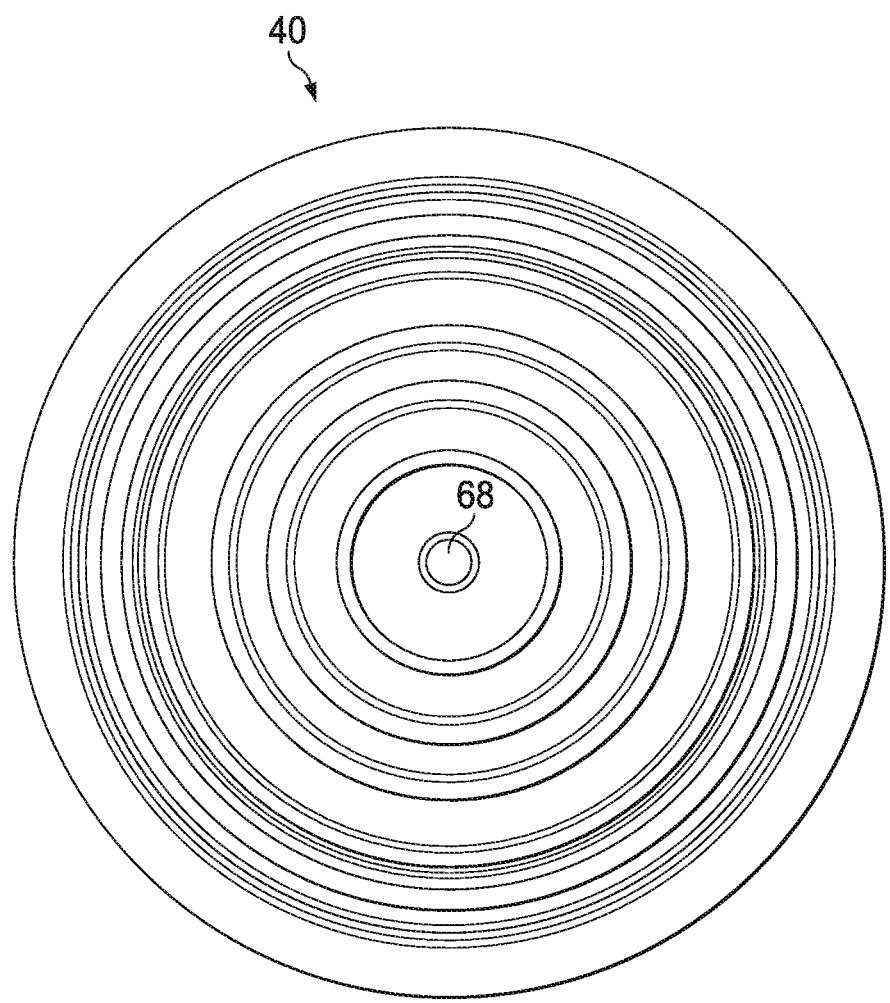
FIG. 9 is a bottom view of the vaginal insert device of FIG. 6A.
Figure 10:
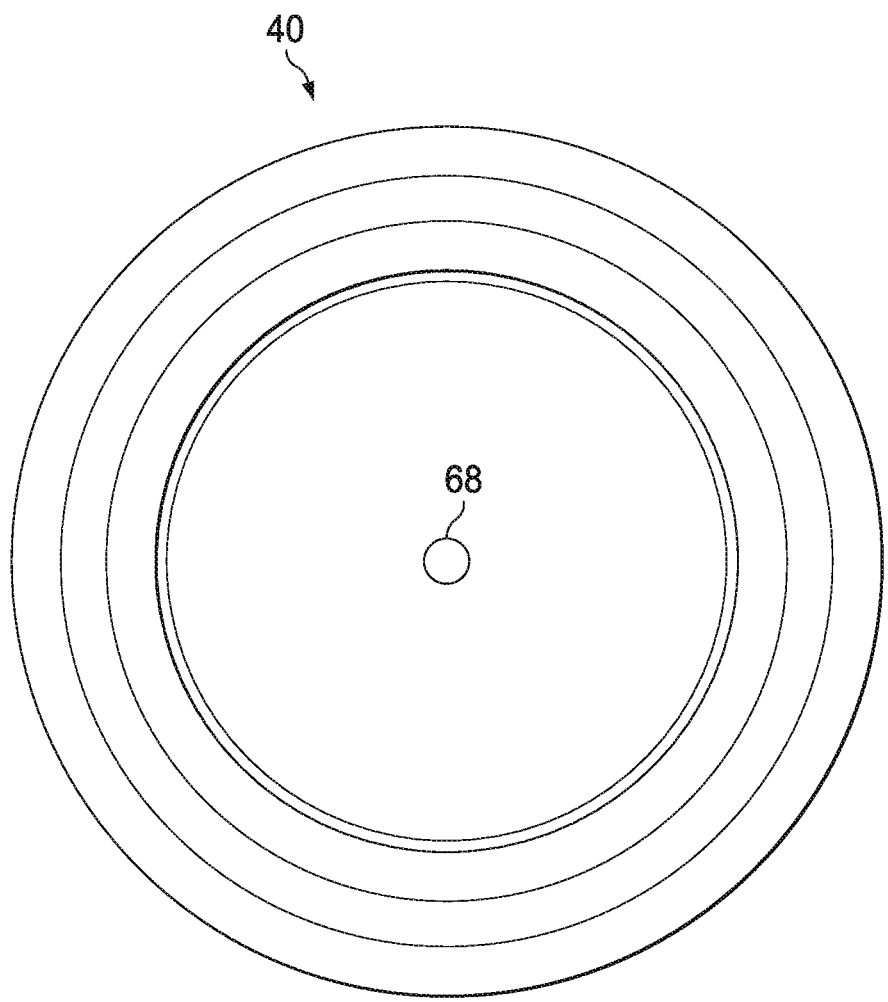
FIG. 10 is a top view of the vaginal insert device of FIG. 6A.

FIG. 9 is a bottom view of the vaginal insert device 40 of FIG. 6A for an embodiment having ventilation opening 68. FIG. 10 is a top view of the vaginal insert device 40 of FIG. 6A for an embodiment having ventilation opening 68.

Figure 11:
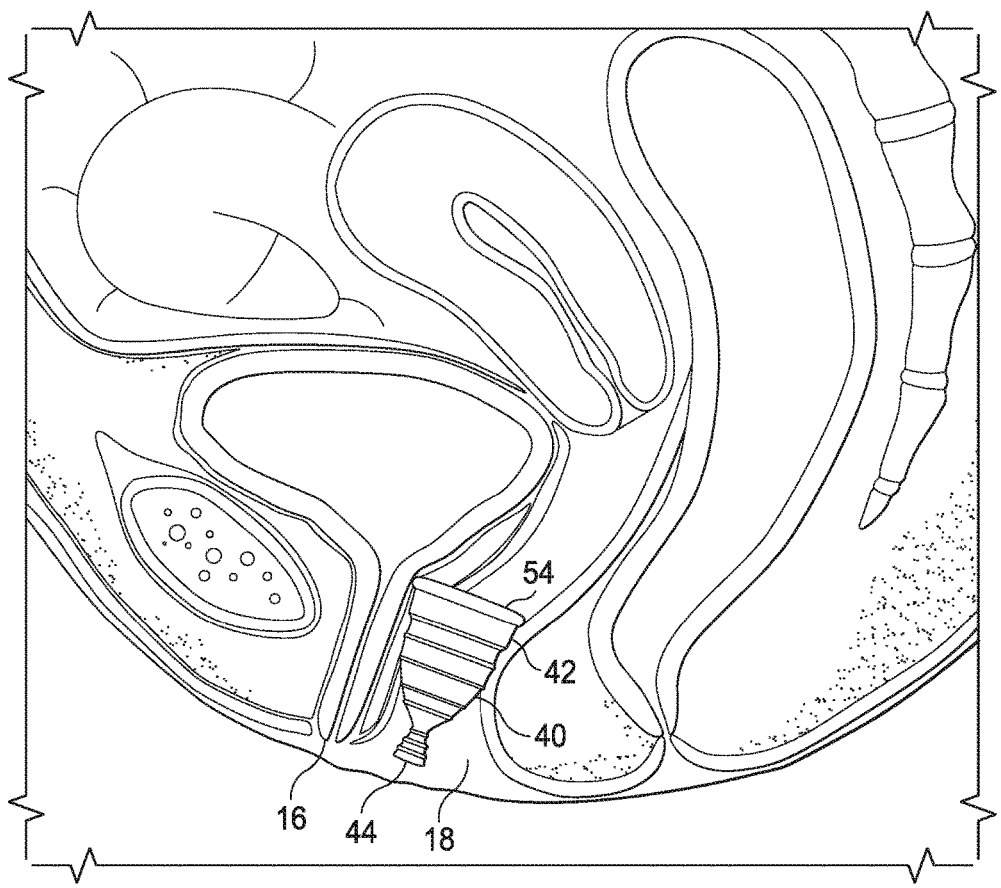
FIGS. 11-13 each illustrate a cross-section of the pelvic region of a female as well as an embodiment of the vaginal insert device inserted in the vagina.
Figure 12:
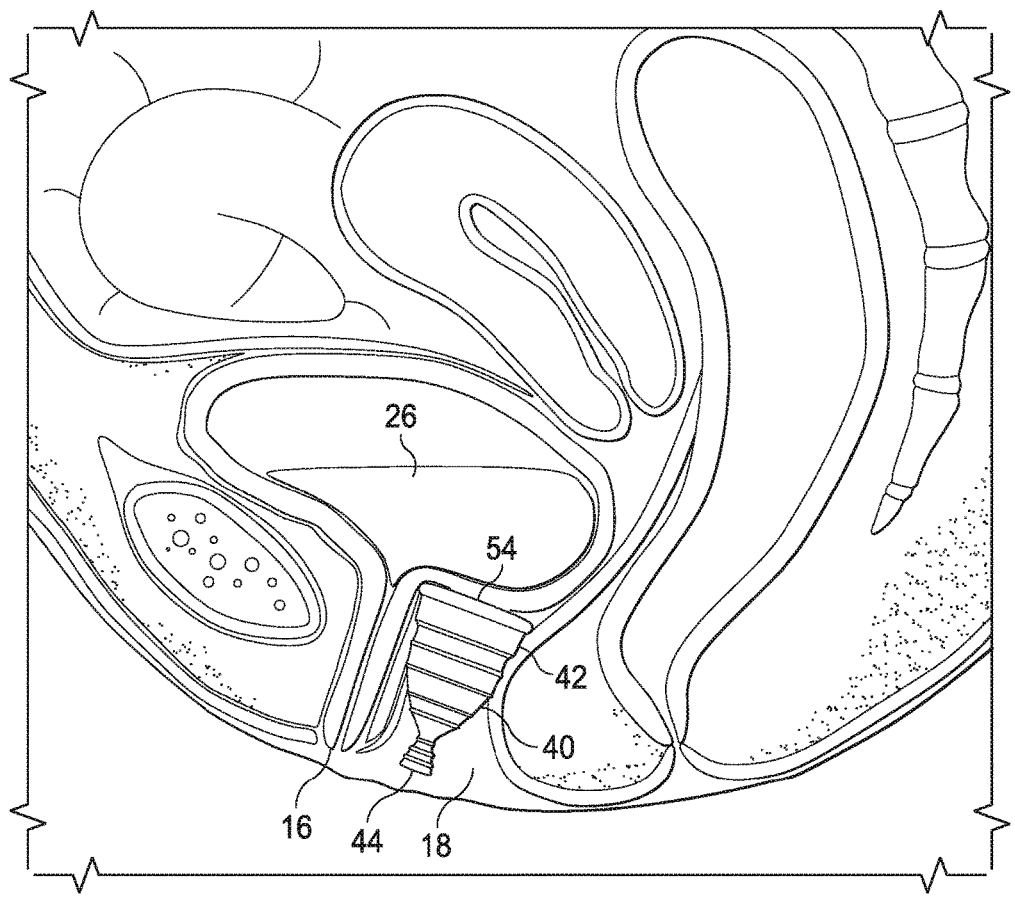
Figure 13:
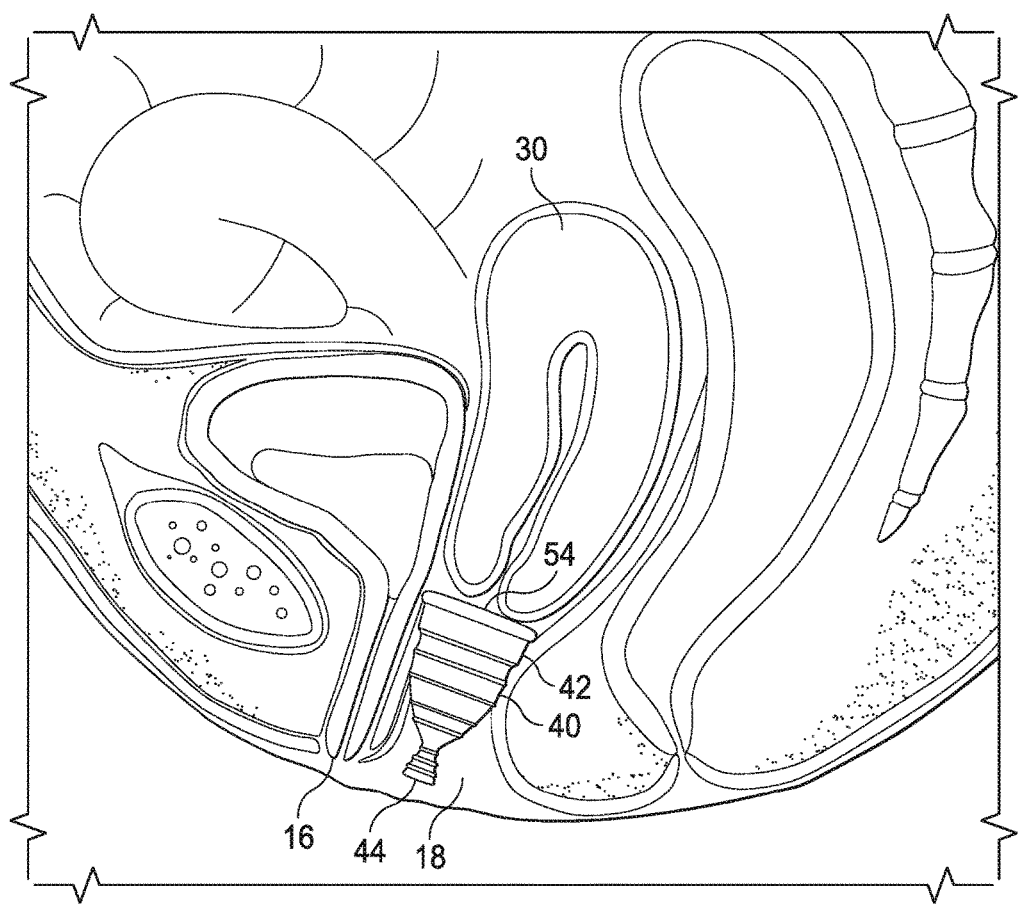

FIG. 11 is a cross-section of the pelvic region of a female illustrating an embodiment of the vaginal insert device 40 inserted in the vagina 18 and applying pressure on the urethral sphincter 16 to manage, improve, or eliminate female urinary incontinence. FIGS. 12 and 13 are each a cross-section of the pelvic region of a female illustrating an embodiment of the vaginal insert device 40 inserted in the vagina 18 to manage, improve, or eliminate POP, in addition to applying pressure on the urethral sphincter 16 to manage, improve, or eliminate female urinary incontinence. In particular, in FIG. 12, vaginal insert device 40 is inserted in the vagina 18 to manage, improve, or eliminate a prolapsed bladder 26. In particular, in FIG. 13, vaginal insert device 40 is inserted in the vagina 18 to manage, improve, or eliminate a prolapsed uterus 30. As illustrated in FIGS. 11-13, the upper open end 54 of the upper portion 42 is the innermost portion of the vaginal insert device 40 during insertion. As further illustrated in FIGS. 11-13, the removal portion or stem 44 of an embodiment of vaginal insert device 40 can be accessed from the exterior of the vagina 18 when the vaginal insert device is inserted and assists in removal of the vaginal insert device. Ridges 48 on stem 44 provide better grip for removal of the device 40 by a patient.

Figure 14A:
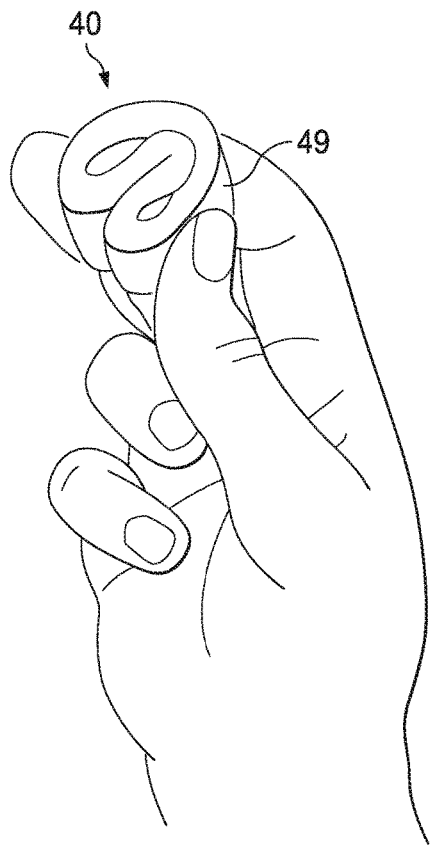
FIGS. 14A and 14B illustrate a method for inserting an embodiment of the vaginal insert device into a patient's vagina.
Figure 14B:
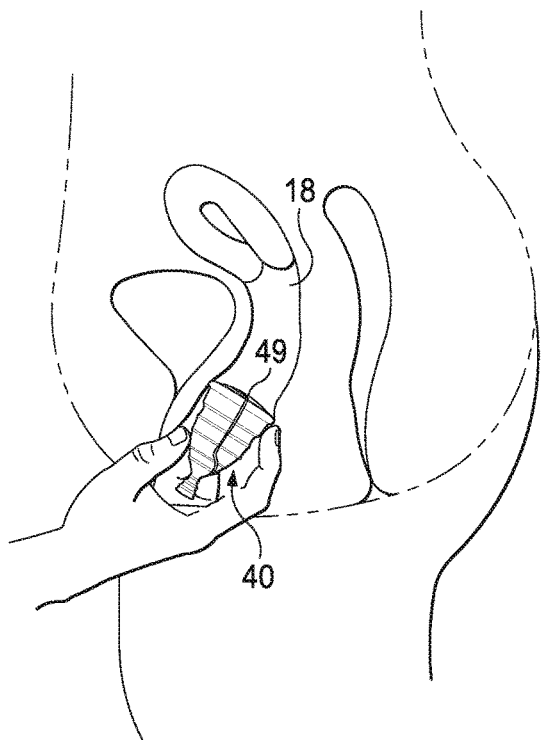

FIGS. 14A and 14B illustrate a method for comfortably inserting vaginal insert device 40 into vagina 18. As illustrated in FIG. 14A, a patient can manually squeeze the wall 49 of the upper portion to make the upper portion more compact for easier insertion of the vaginal insert device 40. As illustrated in FIG. 14B, once vaginal insert device 40 is manually inserted into vagina 18, wall 49 expands back to its original shape.

Figure 15C:
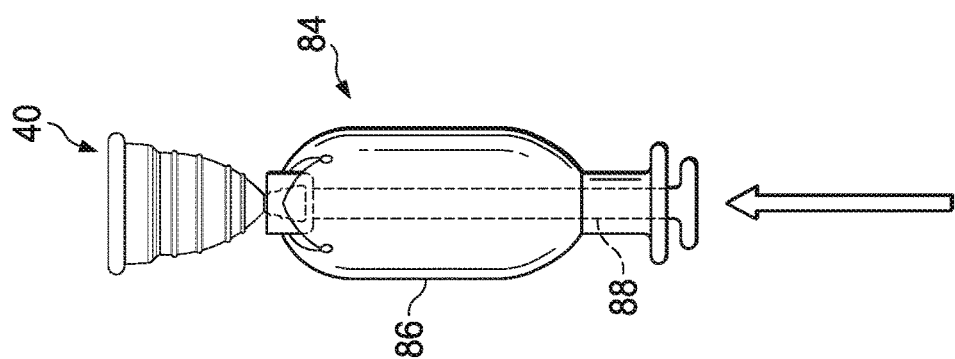
FIGS. 15B-15C illustrate a cross-section of the pessary applicator of FIG. 15A, and a method of using the same to insert an embodiment of the vagina insert device into a patient's vagina.
Figure 15B:
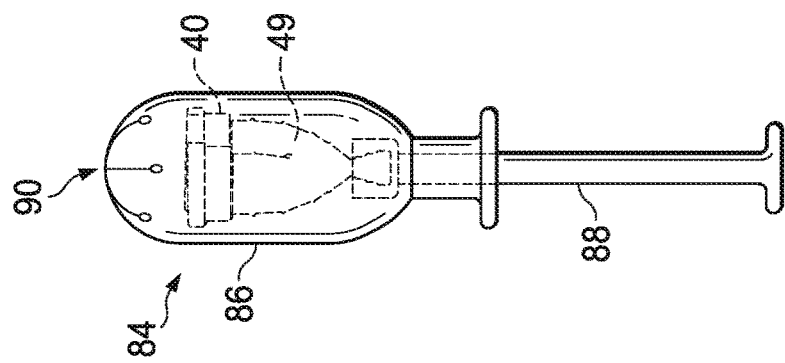
Figure 15A:
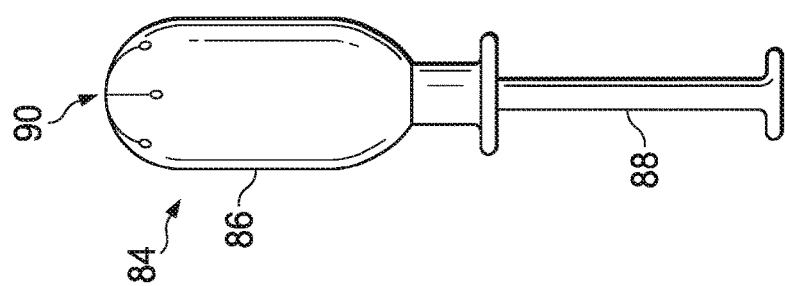
FIG. 15A illustrates a side-view of a pessary applicator.

FIG. 15A illustrates a side-view of a pessary applicator 84 which can be used to assist in inserting a vaginal insert device 40 into a patient's vagina 18. Pessary applicator 84 comprises an insertion member 86, a top portion 90 of the insertion member, and a plunger 88. Pessary applicator 84 is generally similar to a tampon applicator. However, the insertion member 86 will generally have a greater circumference than a tampon applicator to accommodate a vaginal insert device 40, which when compacted has a shape which is generally larger than the circumference of a tampon. FIGS. 15B-15C illustrate a cross-section of the pessary applicator 84 of FIG. 15A, and a method of using the applicator to comfortably insert a vaginal insert device 40 into a patient's vagina 18. As is illustrated, vagina insert device 40 is housed inside insertion member 86 in a compacted shape. Similar to the process of insertion of a tampon into a vagina using an applicator, insertion member 86 of applicator 84 is inserted into the patient's vagina 18, and the plunger 88 is pushed towards the insertion member, ejecting the vaginal insert device 40 through the top portion 90. The applicator 84 is then removed from the vagina 18, and the vaginal insert device 40 remains in place in the vagina, expanded back to its normal shape. The vaginal insert device 40 which has been inserted is positioned such as is illustrated in FIG. 11.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus, device or system or a component, section, or portion of an apparatus, device or system being adapted to, arranged to, capable of, configured to, enabled to, operable to, or operative to perform a particular function encompasses that apparatus, device, system, or component, whether or not it or that particular function is used, activated, turned on, or unlocked, as long as that apparatus, system, device or component is so adapted, arranged, capable, configured, enabled, operable, or operative.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

What is claimed is:

1. A vaginal insert device, comprising:
   an upper portion, which is made of an elastic and non-absorbent material, having a cone-shaped body, having a circular transverse cross-section throughout a length of the upper portion, having a wall with an interior side and an exterior side, an upper open end, a lower end, and a hollow interior, wherein a circumference of the upper portion decreases from the upper open end to the lower end, wherein the upper open end of the upper portion is the innermost portion of the vaginal insert device during insertion, and wherein the wall of the upper portion is configured to be squeezed to make the upper portion into a more compact shape for easier insertion of the vaginal insert device, and wherein said wall expands back to its original shape after the insertion;
   an exterior rim surrounding and protruding from the exterior side of the wall of the upper portion, the exterior rim being adjacent to said upper open end;
   a plurality of ridges surrounding and protruding from the exterior side of the wall of the upper portion, the plurality of ridges being spaced apart from the upper open end to the lower end;
   wherein said upper portion, with said exterior rim and said plurality of ridges, holds the vaginal insert device securely in place to impose pressure on the urethral sphincter, or to support pelvic organs, or to both impose pressure on the urethral sphincter and support pelvic organs, when the device is inserted; and
   a removal portion extending from said lower end of said upper portion, wherein the removal portion is configured to be accessed from the exterior of a vagina when the vaginal insert device is inserted in said vagina, and wherein said removal portion assists in removal of the vaginal insert device,
   wherein the vaginal insert device manages, improves, or eliminates pelvic organ prolapse, urinary incontinence, or both pelvic organ prolapse, and urinary incontinence, or the vaginal insert device is for use in improving symptoms associated with pelvic organ prolapse urinary incontinence, or both pelvic organ prolapse and urinary incontinence.

2. The vaginal insert device of claim 1, wherein said material is a biocompatible elastomer.

3. The vaginal insert device of claim 2, wherein said material is a silicone elastomer.

4. The vaginal insert device of claim 1, wherein the removal portion is a string attached to said upper portion.

5. The vaginal insert device of claim 1, wherein the removal portion is a stem attached to said upper portion.

6. The vaginal insert device of claim 5, wherein the upper portion and the stem comprise an integral one-piece device made from said elastic and non-absorbent material.

7. The vaginal insert device of claim 1, further comprising at least one ventilation opening.

8. The vaginal insert device of claim 1, further comprising an applicator used during the insertion of the device, wherein the applicator is configured to house at least the upper portion when the upper portion is in said more compact shape, and wherein the applicator assists in the insertion of the device.

9. The vaginal insert device of claim 1, wherein said exterior rim is circular and has a first section and a second section, and wherein said first section protrudes from the exterior side of the wall of the upper portion a greater distance than the second section.

10. The vaginal insert device of claim 1, wherein the vaginal insert device is configured to equalize air pressure between an inside and an outside of the vagina, when the vaginal insert device is inserted.

11. A vaginal insert device for use in improving symptoms associated with pelvic organ prolapse, urinary incontinence, or both pelvic organ prolapse and urinary incontinence, comprising:
an upper portion, which is made of an elastic and non-absorbent material, having a cone-shaped body, having a circular transverse cross-section throughout a length of the upper portion, having a wall with an interior side and an exterior side, an upper open end, a lower end, and a hollow interior, wherein a circumference of the upper portion decreases from the upper open end to the lower end, wherein the upper open end of the upper portion is the innermost portion of the vaginal insert device during insertion, and wherein the wall of the upper portion is configured to be squeezed to make the upper portion into a more compact shape for easier insertion of the vaginal insert device, and wherein said wall expands back to its original shape after the insertion;
an exterior rim surrounding and protruding from the exterior side of the wall of the upper portion, the exterior rim being adjacent to said upper open end;
a plurality of ridges surrounding and protruding from the exterior side of the wall of the upper portion, the plurality of ridges being spaced apart from the upper open end to the lower end, wherein the plurality of ridges are distributed along an entire length of the upper portion from the lower end to the exterior rim;
wherein said upper portion, with said exterior rim and said plurality of ridges, hold the vaginal insert device securely in place to impose pressure on the urethral sphincter, or to support pelvic organs, or to both impose pressure on the urethral sphincter and support pelvic organs, when the device is inserted; and
a stem extending from said lower end of said upper portion, wherein the upper portion and the stem comprise an integral one-piece device made from said elastic and non-absorbent material, wherein the stem is configured to be accessed from the exterior of a vagina when the vaginal insert device is inserted in said vagina, and wherein said stem assists in removal of the vaginal insert device.

12. The vaginal insert device of claim 11, wherein said material is a biocompatible elastomer.

13. The vaginal insert device of claim 12, wherein said material is a silicone elastomer.

14. The vaginal insert device of claim 11, further comprising at least one ventilation opening in the wall of the upper portion.

15. The vaginal insert device of claim 11, further comprising a ventilation opening located at a point where the lower end of the upper portion and said stem intersect.

16. The vaginal insert device of claim 11, further comprising an applicator used during the insertion of the device, wherein the applicator is configured to house at least the upper portion when the upper portion is in said more compact shape, and wherein the applicator assists in the insertion of the device.

17. The vaginal insert device of claim 11, wherein said exterior rim has a first section and a second section, and wherein said first section protrudes from the exterior side of the wall of the upper portion a greater distance than the second section.

18. The vaginal insert device of claim 11, wherein the vaginal insert device manages, improves, or eliminates pelvic organ prolapse, urinary incontinence, or both pelvic organ prolapse and urinary incontinence.

19. The vaginal insert device of claim 11, wherein the plurality of ridges hold the device securely in place and impose pressure on at least one vaginal organ.

20. The vaginal insert device of claim 11, wherein the plurality of ridges are uniformly distributed from the lower end of the upper portion to the rim of the upper portion.

21. The vaginal insert device of claim 11, wherein the exterior rim is circular.

22. The vaginal insert device of claim 11, wherein the vaginal insert device is configured to equalize air pressure between an inside and an outside of the vagina, when the vaginal insert device is inserted.

23. A vaginal insert device, comprising:
an upper portion, which is made of elastic, non-absorbent, biocompatible silicone elastomer material, having a cone-shaped body, having a circular transverse cross-section throughout a length of the upper portion, having a wall with an interior side and an exterior side, an upper open end, a lower end, and a hollow interior, wherein a circumference of the upper portion decreases from the upper open end to the lower end, wherein the upper open end of the upper portion is the innermost portion of the vaginal insert device during insertion, and wherein the wall of the upper portion is configured to be squeezed to make the upper portion into a more compact shape for easier insertion of the vaginal insert device, and wherein said wall expands back to its original shape after the insertion;
an exterior rim surrounding and protruding from the exterior side of the wall of the upper portion, the exterior rim being adjacent to said upper open end;
a plurality of ridges surrounding and protruding from the exterior side of the wall of the upper portion, the plurality of ridges being spaced apart from the upper open end to the lower end;
wherein said upper portion, with said exterior rim and said plurality of ridges, hold the vaginal insert device securely in place to impose pressure on the urethral sphincter, or to support pelvic organs, or to both impose pressure on the urethral sphincter and support pelvic organs, when the device is inserted;
a stem extending from said lower end of said upper portion, wherein the upper portion and the stem comprise an integral one-piece device made from said silicone, wherein the stem is configured to be accessed from the exterior of a vagina when the vaginal insert device is inserted in said vagina, and wherein said stem assists in removal of the vaginal insert device; and
a ventilation opening,
wherein the vaginal insert device is configured to equalize air pressure between an inside and an outside of the vagina, when the vaginal insert device is inserted, and wherein the vaginal insert device manages, improves, or eliminates pelvic organ prolapse, urinary incontinence, or both pelvic organ prolapse and urinary incontinence, or the vaginal insert device is for use in improving symptoms associated with pelvic organ prolapse, urinary incontinence, or both pelvic organ prolapse and urinary incontinence.

24. The vaginal insert device of claim 23, wherein a circumference of the upper open end of the upper portion is greater than a circumference of the stem.

25. The vaginal insert device of claim 23, further comprising the ventilation opening located in the wall of the upper portion.

26. The vaginal insert device of claim 10, wherein the ventilation opening is located in the rim.

27. The vaginal insert device of claim 10, wherein the ventilation opening has a diameter of about 2.0 mm.

28. The vaginal insert device of claim 23, further comprising an applicator used during the insertion of the device, wherein the applicator is configured to house at least the upper portion whoa the upper portion is in said more compact shape, and wherein the applicator assists in the insertion of the device.

29. The vaginal insert device of claim 23, wherein said exterior rim has a first section and a second section, and wherein said first section protrudes from the exterior side of the wall of the upper portion a greater distance than the second section.

30. The vaginal insert device of claim 23, further comprising the ventilation opening located at a point where the lower end of the upper portion and the stem intersect.

31. The vaginal insert device of claim 23, wherein the vaginal insert device is configured for use in improving symptoms associated with pelvic organ prolapse, urinary incontinence, or both pelvic organ prolapse and urinary incontinence without fluid collection.

* * * * *

UNITED STATES PATENT AND TRADEMARK OFFICE
CERTIFICATE OF CORRECTION

PATENT NO. : 10,188,545 B2
APPLICATION NO. : 15/242105
DATED : January 29, 2019
INVENTOR(S) : Allison Conti Page 1 of 1

It is certified that error appears in the above-identified patent and that said Letters Patent is hereby corrected as shown below:

In the Claims

- Claim 26, replace "The vaginal insert device of claim 10, wherein the ventilation opening is located in the rim." with -- The vaginal insert device of claim 25, wherein the ventilation opening is located in the rim. --

- Claim 27, replace "The vaginal insert device of claim 10, wherein the ventilation opening has a diameter of about 2.0 mm." with -- The vaginal insert device of claim 25, wherein the ventilation opening has a diameter of about 2.0 mm. --

Signed and Sealed this
First Day of October, 2019

Andrei Iancu
*Director of the United States Patent and Trademark Office*